United States Patent [19]

Pickett

[11] Patent Number: 5,712,419
[45] Date of Patent: Jan. 27, 1998

US005712419A

[54] METHOD OF MAKING COUPLED 4,6-DIBENZOYLRESORCINOLS

[75] Inventor: James Edward Pickett, Schenectady, N.Y.

[73] Assignee: General Electric Company, Schenectady, N.Y.

[21] Appl. No.: 780,031

[22] Filed: Dec. 23, 1996

[51] Int. Cl.[6] ................................................ A61K 35/35
[52] U.S. Cl. ................................................ 568/313
[58] Field of Search ................................................ 568/313

[56] References Cited

U.S. PATENT DOCUMENTS 3,506,610  4/1970  Dressler et al. .................... 568/313

Primary Examiner—James H. Reamer
Attorney, Agent, or Firm—Noreen C. Johnson; William H. Pittman

[57] ABSTRACT

An improved method of making methylene-bridged 4,6-dibenzoylresorcinol dimers in a single step in high yield quantities is provided. The method heats a 4,6-dibenzoylresorcinol (DBR) with a para-aldehyde or an aromatic aldehyde in a carboxylic acid solvent in the presence of a strong acid catalyst.

20 Claims, No Drawings

METHOD OF MAKING COUPLED 4,6-DIBENZOYLRESORCINOLS

FIELD OF THE INVENTION

This invention relates to an improved method of making coupled 4,6-dibenzoylresorcinols. More particularly, the invention relates to making a methylene-bridged dimer of a 4,6-dibenzoylresorcinol in a single step.

BACKGROUND OF THE INVENTION

Thermoplastic substrates such as polycarbonates are generally characterized by many advantageous properties which include clarity, high ductility, high heat deflection temperature, as well as dimensional stability. Many of these materials are transparent and are conventionally employed as replacements for glass in commercial applications. However, they often are susceptible to degradation by ultraviolet light. This results in unfavorable characteristics including yellowing and erosion of the substrate surface.

Recently, it is becoming more and more common for thermoplastic substrates such as polycarbonate to be employed outdoors. It is thus important to impart weatherability properties to the substrate. This is often accomplished by treating the substrate surface with a weather resistant coating material, whereby the coating material typically contains ultraviolet light absorbing agents. Weather resistant coating systems can be prepared by incorporating ultraviolet light absorbers, such as benzotriazoles and benzophenones, and hindered amine light stabilizers. Also, ultraviolet light absorbers are sometimes incorporated into the substrate material itself to impart weatherability properties.

It is often discovered, however, that the ultraviolet light absorbing compounds (herein also referred to as UV absorbers), themselves, decompose upon exposure to ultraviolet light. Prolonged exposure to sunlight, moisture and thermal cycling conditions can cause yellowing, delamination and formation of microcracks in the coating material, decreasing transparency. This leads to a degradation of the favorable properties of the thermoplastic substrate which the UV absorbers are originally employed to protect. Thus, there is an ongoing need to seek new, efficient UV absorbing compounds.

Recently, novel methylene-bridged derivatives of 4,6-dibenzoylresorcinols having a phenol group on the bridging methylene have been discovered and are the subject of co-pending, commonly assigned patent application, U.S. Ser. No. (attorney docket RD-24,624). The claimed compounds are useful as ultraviolet light (UV) absorbers. To make the novel compounds, several steps were taken. An important step was the preparation of a novel intermediate methylene acetate compound. This compound had to be washed and separated from the filtrate and then further mixed with additional 4,6-dibenzoylresorcinol or phenol to form the novel methylene-bridged derivatives of 4,6-dibenzoylresorcinol. Thus, there is a need for an improved, simpler method of making the novel UV absorbers.

SUMMARY OF THE INVENTION

This invention satisfies the need by providing an improved method of making methylene-bridged 4,6-dibenzoylresorcinol dimers in a single step in high yield quantities. The method comprises heating a 4,6-dibenzoylresorcinol (DBR) with a para-aldehyde or an aromatic aldehyde in a carboxylic acid solvent in the presence of a strong acid catalyst. The reaction produces a methylene-bridged 4,6-dibenzoylresorcinol dimer in one step. The formation of the intermediate methylene acetate is eliminated, as is the use of a secondary amine. A preferred para-aldehyde is paraformaldehyde and a preferred carboxylic acid is acetic acid. A high yield is greater than about 60% product, and preferably greater than about 70% product, and most preferably greater than or equal to about 90% product.

In a first aspect, the instant invention is directed to an improved method of making a methylene-bridged dimer of 4,6-dibenzoylresorcinol comprising the step of: heating a mixture of a 4,6-dibenzoylresorcinol and about one-half molar equivalent or greater of an alkyl para-aldehyde or aromatic aldehyde in a solvent at a temperature between about 80°–180° C. for a sufficient amount of time to make a methylene-bridged dimer of 4,6-dibenzoylresorcinol, said 4,6-dibenzoylresorcinol having the formula

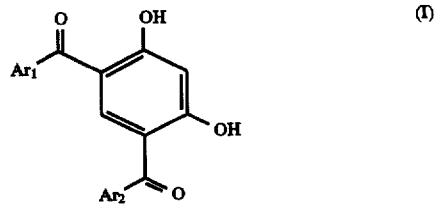

where $Ar_1$ and $Ar_2$ are independently substituted or unsubstituted monocyclic or polycyclic aryl groups, and said methylene-bridged dimer of 4,6-dibenzoylresorcinol having the formula

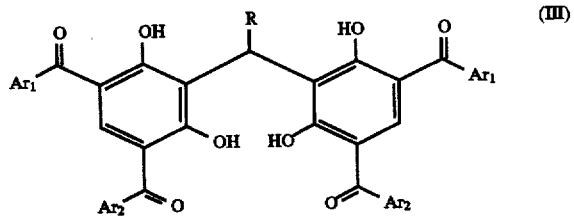

where $Ar_1$ and $Ar_2$ are independently substituted or unsubstituted monocyclic or polycyclic aryl groups, and R is H, an aryl group or a linear or branched alkyl chain having less than about 10 carbons.

Another aspect of this invention is a method for preparing ultraviolet light absorbers, comprising the step of mixing an admixture of a substituted or unsubstituted aryl group on a 4,6-dibenzoylresorcinol, an acid catalyst, an organic solvent, and sufficient para-aldehyde or aromatic aldehyde at a temperature and a time sufficient to form methylene bridged dimers of 4,6-dibenzoylresorcinols.

Those skilled in the art will gain a further and better understanding of the present invention from the detailed description set forth below, considered in conjunction with the examples and chemical drawings accompanying and forming a part of the specification.

DESCRIPTION OF THE INVENTION

It has been discovered that methylene-bridged dimers of 4,6-dibenzoylresorcinal, useful as UV absorbers, can be made in high yield in one step. This invention demonstrates this by preparing bis(2,6-dihydroxy-3,5-dibenzoylphenyl) methane in a single step in high yield by heating 4,6-dibenzoylresorcinol with paraformaldehyde in acetic acid in the presence of a strong acid catalyst. Also, bis(2,6-dihydroxy-3,5-dibenzoylphenyl)phenylmethane can be prepared in a single step by heating 4,6-dibenzoylresorcinol in excess aromatic aldehyde and acid catalyst.

A simple one-step procedure that produces a very high yield of the desired methylene-bridged product in a single step is shown in Scheme 1. A substituted or unsubstituted 4,6-dibenzoylresorcinol derivative is heated between about 80° C. to reflux temperature, and preferably between about 80°–150° C., with slightly more than one-half molar equivalent of an alkyl para-aldehyde or an aromatic aldehyde and an acid catalyst in an appropriate solvent.

Scheme 1.

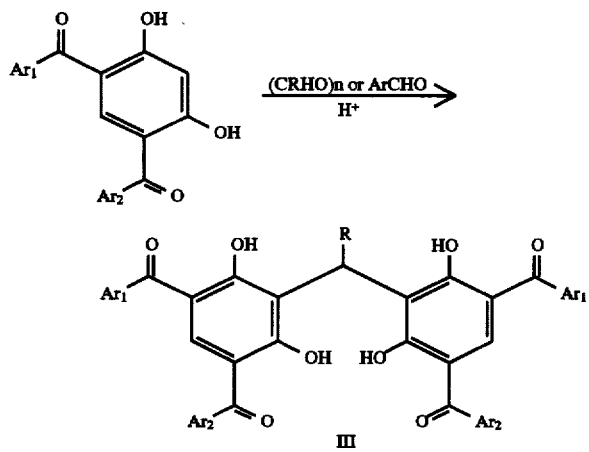

Ar₁ and Ar₂ are independently substituted or unsubstituted monocyclic or polycyclic aryl groups, and R is H, an aryl group or a linear or branched alkyl chain having less than about 10 carbons. The scope of the reaction includes all possible substitutions on the phenyl rings of the starting dibenzoylresorcinol. In addition, one is able to carry out the reaction in a variety of carboxylic acid solvents, and perhaps other solvents as well, and with a variety of strong acid catalysts.

Acetic acid is an attractive solvent for this application because the starting materials have significant solubility in it, especially at elevated temperatures, while the product precipitates out. A variety of carboxylic acid solvents, such as, but not limited to, acetic acid, propionic acid, hexanoic acid, and the like, may be used.

Mineral acids are used as catalysts. Sulfuric acid works well as the catalyst.

Examples of para-aldehydes (CRHO)ₙ are paraformaldehyde or para acetaldehyde. Also, it is found that it is possible to use aromatic aldehydes to give derivatives with substitutions on the methylene group in the methylene-bridged dimers of 4,6-dibenzoylresorcinol. There should be no limitation on the structure of the aromatic aldehyde. Examples of aromatic aldehydes (ArCHO) are benzaldehyde, the various tolualdehydes, anisaldehydes, and the like. In the case of using an aromatic aldehyde, the reaction runs in an excess of the aldehyde and no additional solvent may be needed.

In another aspect of the invention, a mixture of dibenzoylresorcinol derivatives can be used as the starting material to give a product containing a mixture of products containing unsymmetrically substituted methylene-bridged derivatives as shown in Structure IV where Ar₁, Ar₂, Ar₃, Ar₄ are independently substituted or unsubstituted aromatic rings and R is H, C1 to C12 alkyl, or an aryl group.

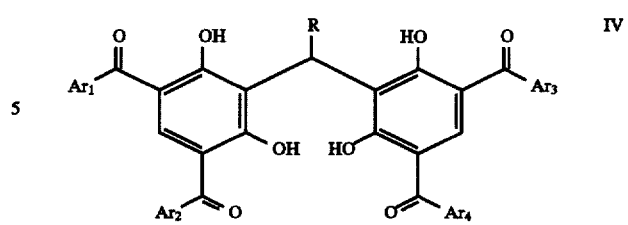

The following examples further serve to demonstrate the invention while not limiting its scope.

EXAMPLE 1

Preparation of compound III'; R=Phenyl 4,6-Dibenzoylresorcinol (6.36 grams, 20 mmol) and 5 drops of concentrated sulfuric acid were added to 20 milliliters of benzaldehyde. The mixture was heated at about 170° C. and stirred for about 24 hours afterwhich the excess benzaldehyde was distilled at reduced pressure. The resulting oil was taken up in ethanol and cooled to yield a dark mass. The solid was placed in a Soxhlet extractor and extracted with hot ethanol for about 2 days. Evaporation of the resulting ethanol solution gave 4.9 grams (68% yield) of a yellow-orange solid. The formula for compound III' is

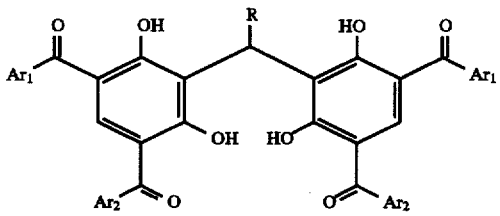

where Ar₁=Ar₂=R=phenyl.

EXAMPLE 2

Preparation of compound III"; R=H 4,6-Dibenzoylresorcinol (1590 grams, 5 moles) and paraformaldehyde (80 grams, 2.67 moles) were suspended in 2000 milliliters of glacial acetic acid in a 5 liter round bottomed flask equipped with an overhead stirrer, reflux condenser, thermometer, and heating mantle. Concentrated sulfuric acid (8.0 grams, 0.08 mole) was added, and the temperature was brought to 115° C. to make a homogeneous solution. Subsequently solid began to form, and 250 milliliters of glacial acetic acid were added to facilitate stirring. After 5 hours the solution was cooled, filtered, and the filter cake washed with acetic acid and then with 2-propanol. The filter cake was then taken up again in hot acetic acid, cooled, filtered, and washed as before. The product was dried at 110° C. in a vacuum oven to give 1449.9 grams (89.5%) of a light yellow solid. Nuclear Magnetic Resonance (NMR) analysis showed it to be identical to bis(2,6-dihydroxy-3,5-dibenzoylphenyl)methane prepared by an independent route. The formula for compound III" is

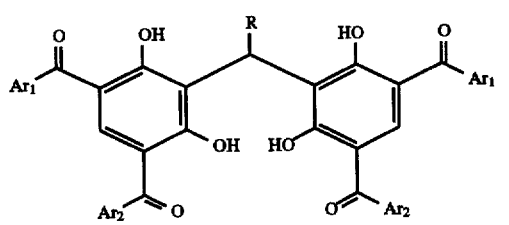

where Ar$_1$ and Ar$_2$=phenyl, and R=H.

EXAMPLE 3

Preparation of mixed methylene-coupled DBR derivatives: compound III''', R=H+compound V+compound VI 4,6-Dibenzoylresorcinol (3.18 grams, 10 mmol), 4,6-di-(4-tert-butylbenzoyl)resorcinol (4.90 grams, 10 mmol) paraformaldehyde (0.48 grams, 16 mmol), and 3 drops of concentrated sulfuric acid were combined in 25 milliliters of glacial acetic acid. The reaction mixture was heated under reflux and stirred for about 7 hours whereupon it was cooled, diluted with 2-propanol and water, filtered, and dried in air to give a product (6.33 grams, 83%) which NMR and mass spectral analysis revealed to be a mixture of compound III''', R=H, compound V and compound VI.

What is claimed:

1. An improved method of making a methylene-bridged dimer of a 4,6-dibenzoylresorcinol comprising the step of:

heating a mixture of a 4,6-dibenzoylresorcinol and about one-half molar equivalent or greater of an alkyl para-aldehyde or aromatic aldehyde with an acid in a solvent at a temperature between about 80° C. and reflux for a sufficient amount of time to make a methylene-bridged dimer of 4,6-dibenzoylresorcinol, said 4,6-dibenzoylresorcinol having the formula

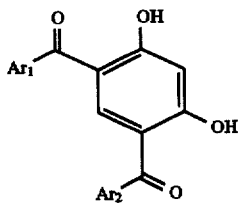

where Ar$_1$ and Ar$_2$ are independently substituted or unsubstituted monocyclic or polycyclic aryl groups, and said methylene-bridged dimer of 4,6-dibenzoylresorcinol having the formula

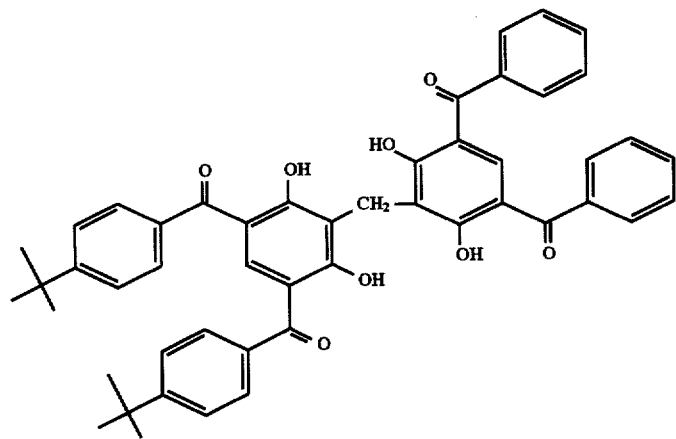

Compound V

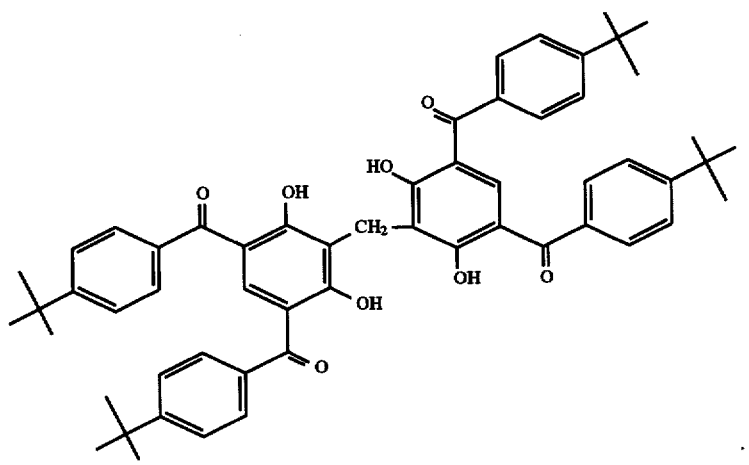

Compound VI.

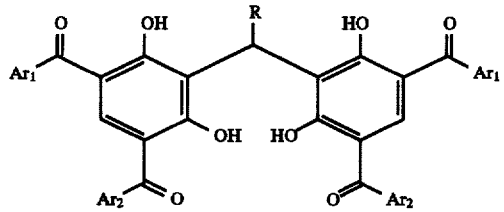

where $Ar_1$ and $Ar_2$ are independently substituted or unsubstituted monocyclic or polycyclic aryl groups, and R is H, an aryl group or a linear or branched alkyl chain having less than about 10 carbons.

2. An improved method of making a methylene-bridged dimer of a 4,6-dibenzoylresorcinol according to claim 1 where the temperature is about 80°–180° C.

3. An improved method of making a methylene-bridged dimer of a 4,6-dibenzoylresorcinol according to claim 1 where the alkyl para-aldehyde is paraformaldehyde.

4. An improved method of making a methylene-bridged dimer of a 4,6-dibenzoylresorcinol according to claim 1 where the aromatic aldehyde is benzaldehyde.

5. An improved method of making a methylene-bridged dimer of a 4,6-dibenzoylresorcinol according to claim 1 where the solvent is a carboxylic acid.

6. An improved method of making a methylene-bridged dimer of a 4,6-dibenzoylresorcinol according to claim 5 where the solvent is acetic acid.

7. An improved method of making a methylene-bridged dimer of a 4,6-dibenzoylresorcinol according to claim 1 where the acid is sulfuric acid.

8. An improved method of making a methylene-bridged dimer of a 4,6-dibenzoylresorcinol according to claim 3 where the methylene-bridged dimer of 4,6-dibenzoylresorcinol has the formula

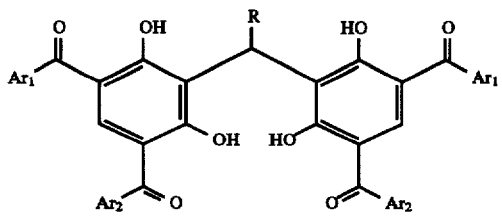

where $Ar_1$ and $Ar_2$ are independently substituted or unsubstituted monocyclic or polycyclic aryl groups, and R is H, or a linear or branched alkyl chain having less than about 10 carbons.

9. An improved method of making a methylene-bridged dimer of a 4,6-dibenzoylresorcinol according to claim 8 where the methylene-bridged dimer of 4,6-dibenzoylresorcinol is bis(2,6-dihydroxy-3,5-dibenzoylphenyl)methane.

10. An improved method of making a methylene-bridged dimer of a 4,6-dibenzoylresorcinol according to claim 4 where the methylene-bridged dimer of 4,6-dibenzoylresorcinol has the formula

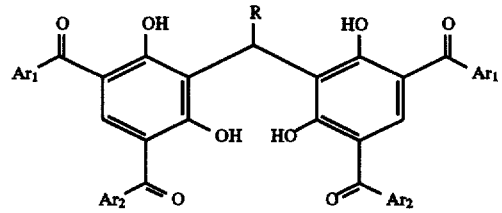

where $Ar_1 = Ar_2 = R = phenyl$.

11. An improved method of making a methylene-bridged dimer of a 4,6-dibenzoylresorcinol according to claim 10 where the methylene-bridged dimer of 4,6-dibenzoylresorcinol is bis(2,6-dihydroxy-3,5-dibenzoylphenyl)phenylmethane.

12. An improved method of making a methylene-bridged dimer of a 4,6-dibenzoylresorcinol according to claim 1 where the solvent is excess aromatic aldehyde.

13. A method for preparing ultraviolet light absorbers, comprising the step of mixing an admixture of a substituted or unsubstituted aryl group on a 4,6-dibenzoylresorcinol, an acid catalyst, an organic solvent, and sufficient para-aldehyde or aromatic aldehyde at a temperature and for a time sufficient to form a methylene bridged dimer of a 4,6-dibenzoylresorcinol.

14. An improved method of making a mixed methylene-coupled DBR derivative comprising the step:

heating a mixture of 4,6-dibenzoylresorcinol derivatives and about one-half molar equivalent or greater of an alkyl para-aldehyde or aromatic aldehyde with an acid in a solvent at a temperature between about 80° C. and reflux for a sufficient amount of time to make unsymmetrical substituted methylene-bridged derivatives having a formula

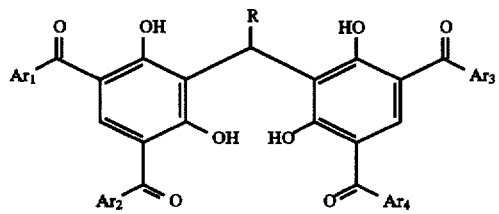

where $Ar_1$, $Ar_2$, $Ar_3$, $Ar_4$ are independently substituted or unsubstituted aromatic rings and R is H, C1 to C12 alkyl, or an aryl group.

15. An improved method of making a mixed methylene-coupled DBR derivative according to claim 14 where the alkyl para-aldehyde is paraformaldehyde.

16. An improved method of making a mixed methylene-coupled DBR derivative according to claim 14 where the aromatic aldehyde is benzaldehyde.

17. An improved method of making a mixed methylene-coupled DBR derivative according to claim 14 where the solvent is a carboxylic acid.

18. An improved method of making a mixed methylene-coupled DBR derivative according to claim 17 where the solvent is acetic acid.

19. An improved method of making a mixed methylene-coupled DBR derivative according to claim 14 where the acid is sulfuric acid.

20. An improved method of making a mixed methylene-coupled DBR derivative according to claim 14 where the solvent is excess aromatic aldehyde.

* * * * *

UNITED STATES PATENT AND TRADEMARK OFFICE
CERTIFICATE OF CORRECTION

PATENT NO. : 5,712,419

DATED : January 27, 1998

INVENTOR(S) : James Edward Pickett

It is certified that error appears in the above-identified patent and that said Letters Patent is hereby corrected as shown below:

Column 2, line 59, cancel "4,6-dibenzyolresorcinal" and substitute --4,6-dibenzoylresorcinol--.

Column 5, line 15, cancel "compound III"" and substitute --compound III"--

Column 5, line 24, cancel "compound III"" and substitute --compound III"--

Signed and Sealed this

First Day of September, 1998

Attest:

BRUCE LEHMAN

Attesting Officer

Commissioner of Patents and Trademarks